United States Patent [19]
Kosuda et al.

[11] Patent Number: 6,155,983
[45] Date of Patent: Dec. 5, 2000

[54] PULSE WAVE DETECTING DEVICE AND PULSE MEASURER

[75] Inventors: Tsukasa Kosuda, Suwa; Chiaki Nakamura, Chiba, both of Japan

[73] Assignees: Seiko Epson Corporation, Tokyo; Seiko Instruments, Inc., Chiba-ken, both of Japan

[21] Appl. No.: 09/180,341
[22] PCT Filed: Mar. 17, 1998
[86] PCT No.: PCT/JP98/01128
  § 371 Date: Nov. 4, 1998
  § 102(e) Date: Nov. 4, 1998
[87] PCT Pub. No.: WO98/41143
  PCT Pub. Date: Sep. 24, 1998

[30] Foreign Application Priority Data

Mar. 17, 1997 [JP] Japan .................................... 9-063487

[51] Int. Cl.⁷ ...................................................... A61B 5/00
[52] U.S. Cl. ........................................... 600/500; 600/485
[58] Field of Search .............................. 600/485, 500–503

[56] References Cited

U.S. PATENT DOCUMENTS

| 5,868,679 | 2/1999 | Miyazaki ............................. 600/500 X |
| 5,873,834 | 2/1999 | Yanagi et al. ......................... 600/500 X |

Primary Examiner—Cary O'Connor
Assistant Examiner—Ryan Carter

[57] ABSTRACT

The present invention relates to a pulse wave detecting device for detecting pulse waves, and to a pulse measurer employing this pulse wave detecting device. The present invention addresses the problem of obtaining a pulse wave signal in which the noise components have been suitably removed from a pulse waveform, and of determining the pulse rate with high accuracy based on this pulse wave signal.

The method for deriving the pulse wave signal and pulse rate is as follows.

The pulse wave signal from pulse wave detecting sensor unit (30) is temporarily stored in buffer (503). When impulse noise is detected in the pulse wave signal in buffer (503) by impulse noise detecting means (505), the band pass for first digital filter (506) becomes a hill-shaped curve centered on the frequency corresponding to the preceding pulse rate, and impulse noise in the pulse wave signal output from buffer (503) is decreased. Thereafter, overall noise and body movement components are decreased in the pulse wave signal by means of second digital filter (507) and third digital filter (508). The signal is then subjected to frequency analysis by frequency analyzer (509), and the pulse rate is calculated from the results of this analysis.

15 Claims, 13 Drawing Sheets

$X_N = (-X_N - X_{N+1} - 4X_{N+2} - X_{N+3} - X_{N+4})/8$ $X_N = (-X_N - X_{N+1} - 8X_{N+2} - X_{N+3} - X_{N+4})/12$

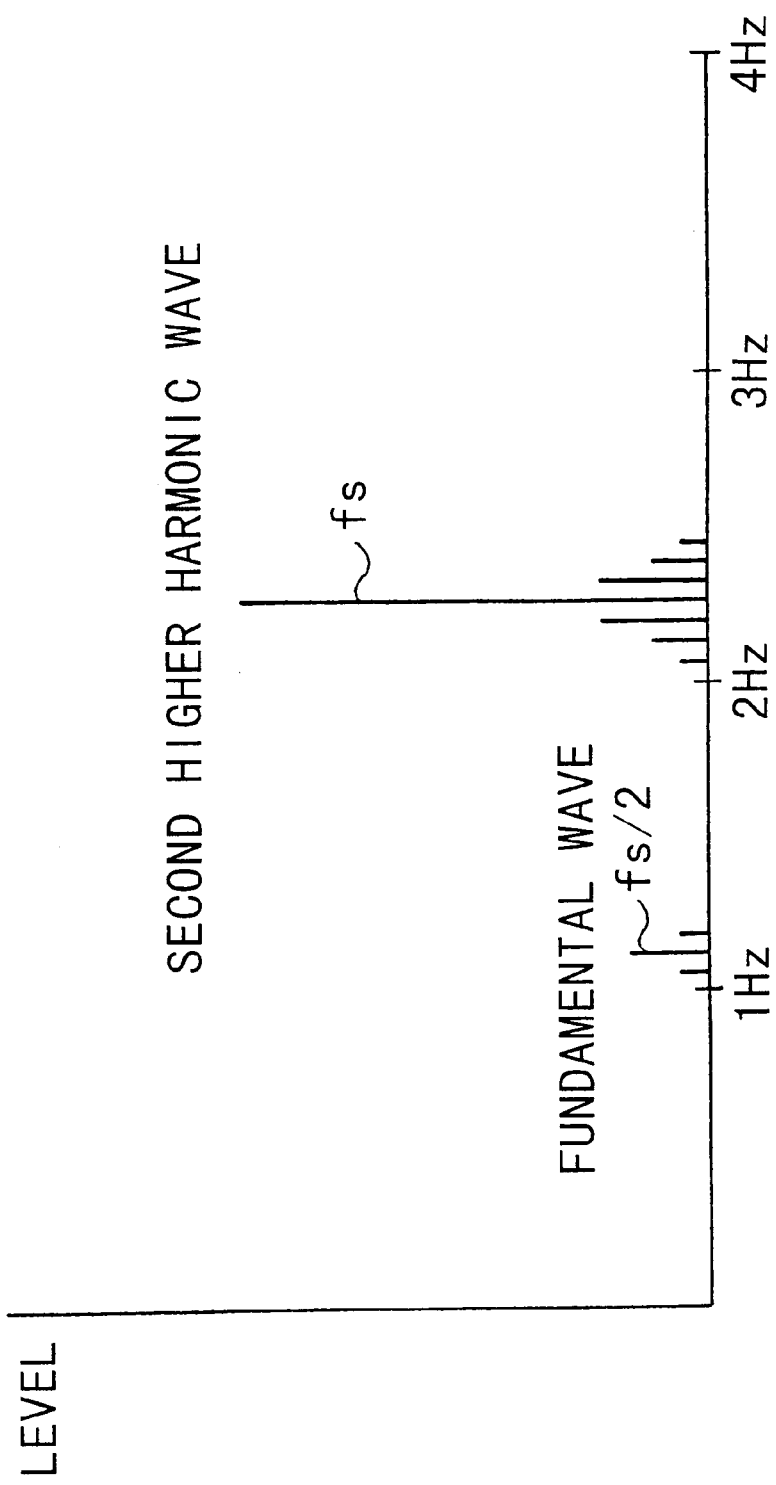

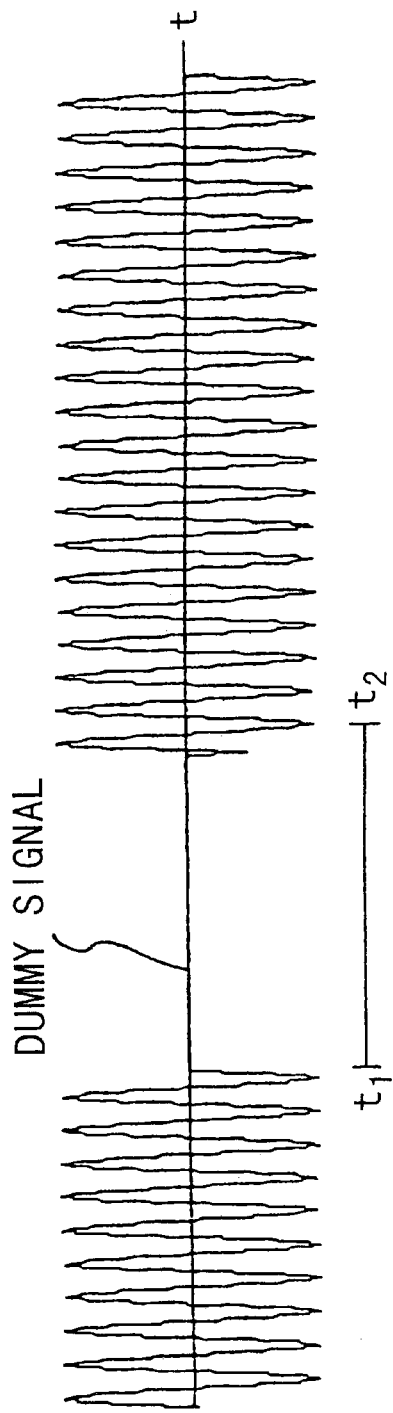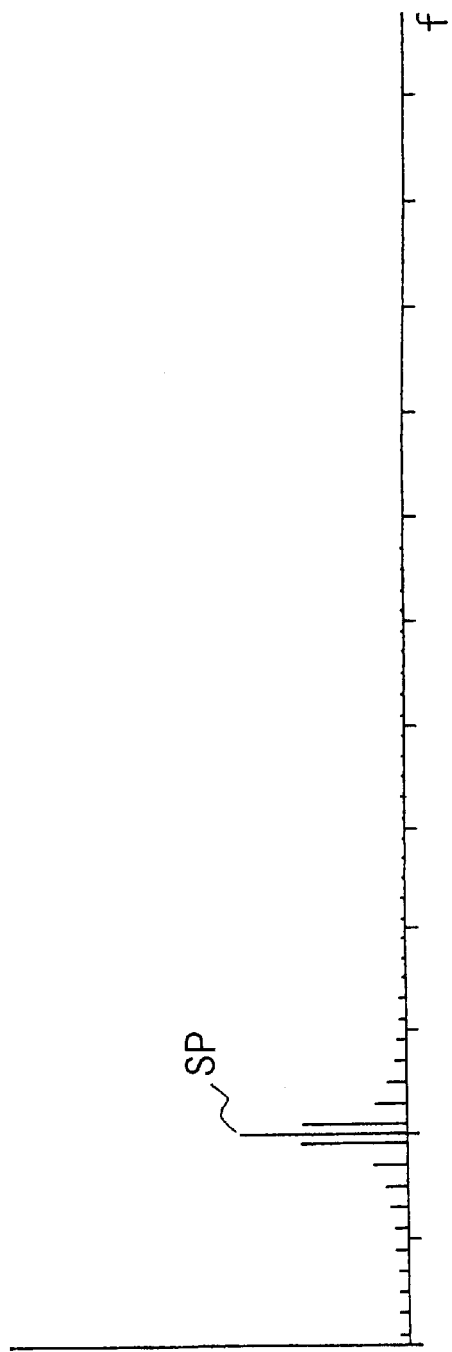

PULSE WAVE DETECTING DEVICE AND PULSE MEASURER

BACKGROUND OF THE INVENTION

1. Field of the Invention

The present invention relates to a pulse wave detecting device for detecting pulse waves, and to a pulse measurer employing the aforementioned pulse wave detecting device.

2. Description of the Related Art

Pulse measurers which detect pulse waves, calculate the pulse rate, and then notify the user of the calculated result have been commercially available for some time. This type of pulse measurer calculates the pulse rate using the signals (pulse wave signals) output from a pulse wave detecting sensor that is disposed near a site on the user's body where the pulse measurement is to be made. Known methods for calculating the pulse rate include the rectangular wave processing method and frequency analysis method described below.

(A) Rectangular wave processing method

In the rectangular wave processing method, the pulse wave signal is converted to a rectangular wave, and the pulse rate is calculated by measuring the period of the rectangular wave (the pulse rate is proportional to the reciprocal of the period). In other words, the pulse rate can be calculated by investigating the variation in the level of the pulse wave signal over a time domain. Thus, this method enables calculation of the pulse rate by only a small amount of calculations and a small-scale circuit structure.

(B) Frequency analysis method

In the frequency analysis method, the pulse wave signal is subjected to frequency analysis, the spectral line having a maximal level is extracted from the spectrum obtained as a result of the frequency analysis, and the pulse rate is calculated from the frequency of this spectral line. In other words, the pulse rate is calculated by comparing the levels of the pulse wave signals within a frequency domain. FFT is typically employed as the frequency analysis method.

However, in addition to the pulse wave components, other noise may be superimposed on the output from the pulse wave detecting sensor. Since this superimposed noise is not necessarily regular, merely providing an analog filter at the input stage does not sufficiently remove its effects. Accordingly, the present inventors have proposed the following processes (1) through (3) for reducing such noise.

(1) Impulse noise removal processing

As used here, impulse noise is the general term for noise which is generated suddenly. An example of a pulse wave signal containing superimposed impulse noise is shown in FIG. 11. FIG. 11(a) shows the pulse wave signal in the time domain, while FIG. 11(b) shows the spectrum obtained after performing an FFT on this pulse wave signal. As is clear from the figures, due to the superimposition of impulse noise, the pulse wave signal is extremely deformed over the time period t1~t2 in FIG. 11(a), and a spectral line is present which is higher than spectral line SP which shows the fundamental wave of the pulse wave. As described above, in the frequency analysis method, the pulse rate is calculated based on the highest level spectral line. Thus, since frequency analysis is performed on the pulse wave signal containing the superimposed impulse noise as shown in the figure, it is not possible to accurately calculate the pulse rate.

Therefore, the present inventors proposed a device which monitors for the presence or absence of phenomena which cause impulse noise to be generated, and when, based on the results of this monitoring, there is a concern that impulse noise may be superimposed, performs frequency analysis after inserting a dummy signal in the interval containing the impulse noise in the pulse signal (for example, time period t1~t2 in FIG. 11(a)) (for details, see specification and figures accompanying Japanese Patent Application No. 273238 of 1995: Japanese Patent First Publication No. 113653 of 1997). In this device, because a dummy signal having a value of 0 is inserted in the time interval t1~t2 in which the impulse noise is superimposed, spectral line SP, which expresses the fundamental wave of the pulse wave, becomes the highest level spectral line in the spectrum obtained as a result of FFT processing. Note that, as is clear from FIGS. 12(a) and 12(b), the above-described device is premised on the use of frequency analysis.

(2) Window processing

Typically, the change in the pulse wave (pulse rate) is continuous, with there being only a slight chance of a large deviation from the previously detected value. Window processing is processing which takes advantage of this fact to set a suitable range (window) for the current detection value by multiplying the value detected previously by a fixed coefficient and, when a detected value outside the range is obtained, which removes this value as an anomalous value resulting from noise. When there is poor following of the pulse rate by the window, then, if the pulse rate changes abruptly such as at the start of exercise (t1) or the like, the pulse rate cannot be followed, as shown in FIG. 13. As a result, a phenomenon occurs in which even if the detected value is a normal value, it is removed as an anomalous value. Moreover, this phenomenon continues until the window is correctly revised. The present inventors have therefore proposed a technique for improving the window's ability to follow the pulse rate (for details, see specification and figures accompanying Japanese Patent Application No. 24511 of 1996: Japanese Patent Application First Publication No. 154825 of 1997).

(3) Processing to remove body motion component

As explained above, the pulse wave detection sensor is typically disposed near the site on the user's body where measurements are to be made. Accordingly, when the user is exercising, a body motion component is superimposed on the pulse wave signal. An example of the spectrum obtained from performing FFT on a pulse wave signal containing a superimposed body motion component is shown in FIG. 14(a). In the example shown in this figure, the spectral lines on the left are the pulse wave components, while the spectral lines on the right are the body motion components. The spectral lines of both these groups are of approximately the same level. Of course, FIG. 14(a) is merely one example, and a situation is also possible in which the highest level spectral line is present among the spectral lines for the body motion component. Accordingly, if frequency analysis is carried out on a pulse wave signal containing a superimposed body motion component, the correct pulse rate cannot be calculated.

Therefore, the present inventors proposed a device comprising a body motion detecting sensor which subtracts the spectrum (14(b)) obtained by performing FFT on the signal (i.e., the body motion signal) output from the body motion detecting sensor from the spectrum shown in FIG. 14(a), and then selects the highest level spectral line after obtaining a spectrum that consists of only pulse wave components such shown in FIG. 14(c) (for details, see Japanese Patent Application No. 227338 of 1995). As is clear from this figure, by means of this device, the selected spectral line is spectral line SP which expresses the fundamental wave of the pulse wave. The device described here is premised on the use of frequency analysis, as should be clear from the fact that spectrum subtraction is carried out.

In the impulse noise removal processing described under (1) above, phenomenon causing impulse noise, for example, features employed in a wristwatch like a flashing back light or a sounding alarm, are set in advance, and a dummy signal is inserted in the pulse wave signal at the time which has been set for the occurrence of these phenomenon. However, general impulse noise may also occur which is not related to the internal state of the device itself, making it extremely difficult to detect all these phenomena. On the other hand, if the device is designed so that a dummy signal is inserted regardless of the generation of such phenomenon, then it is possible to completely remove the impulse noise. However, the essential pulse wave components are also removed entirely. In other words, removal of all the impulse noise while having only a minimal effect on the essential pulse wave components is extremely difficult to accomplish by means of the only the processing described in (1) above.

Moreover, in the case of the window processing described under (2) above, values detected outside the window are removed, so that when changes in the window cannot follow changes in the pulse wave (when an arrhythmia has occurred for example), an accurately detected value is removed as an anomalous value.

Finally, in the body motion component removal processing described under (3) above, spectrum subtraction is carried out. However, because the body motion components (on the left in FIG. 14(a)) in the output from the pulse wave detecting sensor, and the body motion components (FIG. 14(b)) in the output from the body motion detecting sensor do not in fact completely coincide, it is not possible to completely remove the body motion component by subtracting the latter from the former.

SUMMARY OF THE INVENTION

The present invention was conceived in consideration of the above-described circumstance, and has as its first objective the provision of a pulse wave detecting device capable of obtaining a pulse wave signal in which the noise component has been appropriately removed from the pulse waveform. The present invention further has as a second objective the provision of a pulse measurer capable of determining the pulse rate with high accuracy by employing the aforementioned pulse wave detecting device.

In order to resolve the above-described problems, a first construction of the present invention's pulse wave detecting device is provided with a pulse wave detecting sensor for detecting pulse waves and outputting pulse wave signals; a filter having variable characteristics for filtering the pulse wave signal output from said pulse wave detecting sensor and outputting the result; a pulse rate calculating means for calculating the pulse rate based on the pulse wave signal which was filtered by said filter; and a characteristics setting means for setting characteristics of said filter based on the pulse rate calculated by said pulse rate calculating means; wherein the characteristics are set in response to the pulse rate calculated based on said filtered pulse wave signal. Accordingly, it is possible to reduce non-pulse wave components in said filtered pulse wave signal, so that the pulse wave can be detected with even higher accuracy.

The first structure as described above is provided with a buffer for temporarily storing the pulse wave signal output from said pulse wave sensor and then outputting it to said filter; and an impulse noise detecting means for detecting impulse noise from the pulse wave signal that was temporarily stored in said buffer. The characteristics setting means may be designed to set the characteristics of said filter after taking into account the results of detection by said impulse noise detecting means. In this case, for example, said filter carries out selective filtering of the pulse wave signal in which said impulse noise detecting means detected impulse noise, so that the impulse noise component is reduced or removed without any large reduction or removal of the essential pulse wave components.

In the above-described first construction, it is also possible to construct said filter so that a level at which the pulse wave signal passes through said filter gradually becomes lower from a reference frequency to the lower and upper limit frequencies of the fundamental wave of the pulse wave, and to set characteristics of said filter by having said characteristics setting means set the reference frequency. In this case, it is possible to reduce the overall noise components without greatly reducing or removing the essential pulse wave components. Note that the reference frequency is the frequency complying with the preceding pulse rate.

In each of the above-described constructions, it is also possible to design said characteristics setting means so that the characteristics set in said filter are changed in response to the state of change in the pulse rated calculated by said pulse rate calculating means. In this case, it is possible to detect the pulse wave with even greater accuracy.

In addition, it is also acceptable to provide a notifying means for notifying the user of the pulse rate calculated by said pulse rate calculating means to each of the pulse wave detecting devices described above. As a result, it becomes possible to realize a pulse measurer which measures the pulse rate at high accuracy.

In order to resolve the problems described above, a second construction of the present invention's pulse wave detecting device is provided with a pulse wave detecting sensor for detecting the pulse wave and outputting pulse wave signals; a filter having variable characteristics for filtering the pulse wave signal output from said pulse wave detecting sensor and outputting the result; a body motion detecting sensor for detecting body motion and outputting a body motion signal; a pitch calculating means for calculating a pitch of the body motion based on the body motion signal output from said body motion detecting sensor; and a characteristics setting means for setting characteristics of said filter based on the pitch calculated by said pitch calculating means; wherein characteristics are set in said filter in response to the pitch of body motion calculated based on the body motion signal output from said body motion detecting sensor. Accordingly, it is possible to reduce noise components due to body motion in the filtered pulse wave signal, so that it becomes possible to detect the pulse wave with even greater accuracy.

In the second construction described above, said characteristics setting means may be designed so that the characteristic set in said filter are changed in response to the state of change in the pitch calculated by said pitch calculating means. In this case, it is possible to detect the pulse wave with even higher accuracy.

In addition, by providing pulse wave detecting devices of the constructions described above with a pulse rate calculating means for calculating the pulse rate based on the pulse wave signal filtered by said filter, and a notifying means for notifying the user of the pulse rate calculated by said pulse rate calculating means, it is possible to realize a pulse measurer which measures the pulse rate with a high degree of accuracy.

BRIEF DESCRIPTION OF THE FIGURES

FIG. 8 is a figure for explaining processing to determine the frequency of the fundamental wave of body motion in the same pulse measurer.

FIGS. 11(a) and (b) show examples of pulse wave signals in which impulse noise has been superimposed, wherein FIG. 11(a) shows the pulse wave signal in the time domain.

FIG. 12 is a figure for explaining conventional impulse noise removal processing, wherein FIG. 12(a) shows the pulse wave signal in the time domain, and FIG. 12(b) shows the spectrum obtained after performing FFT on the pulse wave signal in FIG. 12(a).

FIGS. 14(a), (b) and (c) are figures for explaining conventional body component removal processing, wherein FIG. 14(a) shows the spectrum obtained after performing FFT processing on a pulse wave signal in which a body motion component is superimposed.

PREFERRED EMBODIMENTS OF THE PRESENT INVENTION

Embodiments of the present invention will now be explained with reference to the accompanying figures. Note that the pulse measurer according to these embodiments is provided with the functions of a regular digital wristwatch, and is employed by switching between a watch mode and a pulse measurer mode.

A: STRUCTURE OF EMBODIMENT

A-1: Overall Structure

Figure 1:
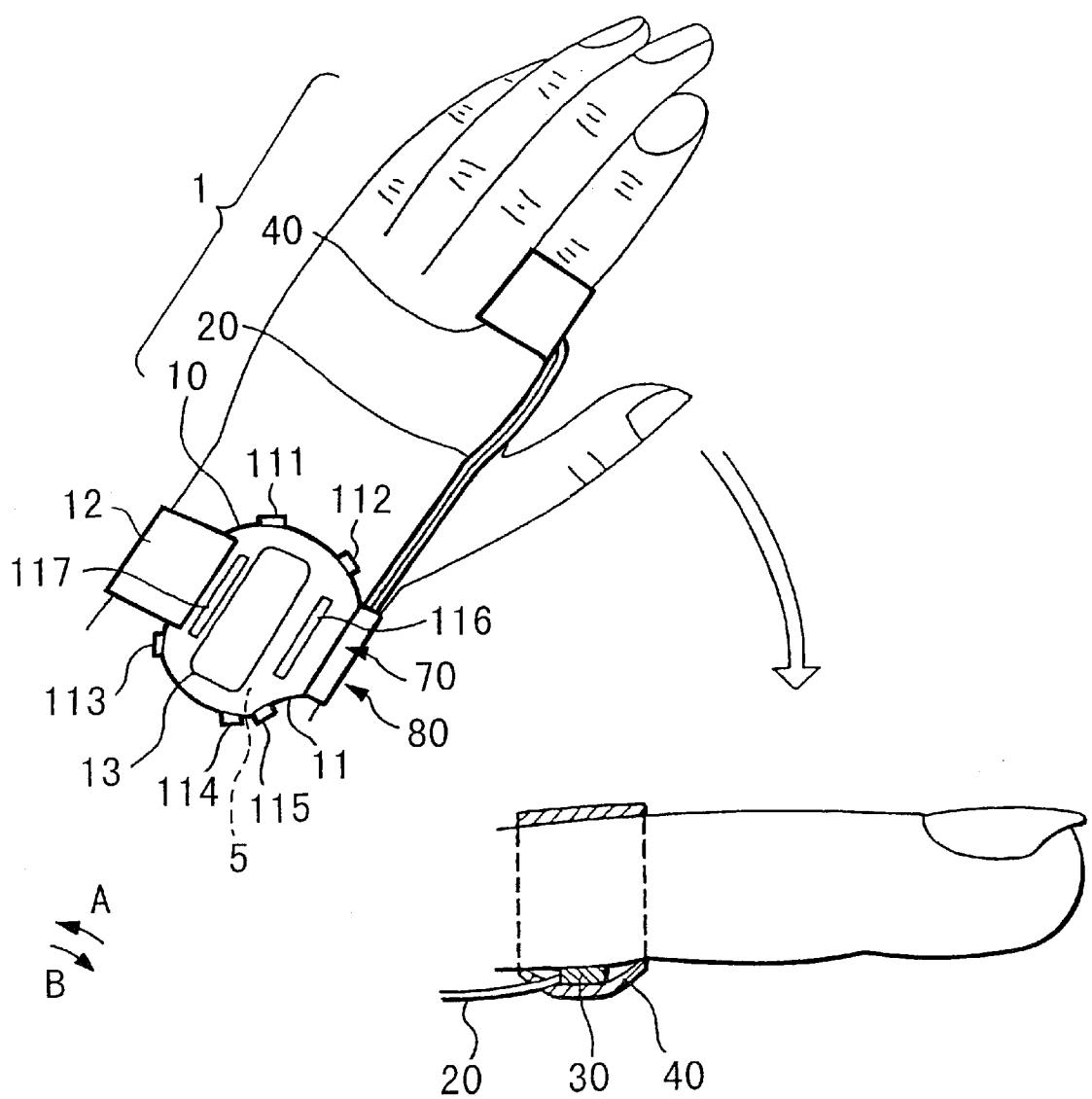
FIG. 1 shows the state of attachment of the pulse measurer in the first embodiment of the present invention.

FIG. 1 shows the state of attachment of the pulse measurer, with the device roughly comprised of a device main body 10 having a wristwatch structure, a cable 20 connected to device main body 10, and a sensor unit 30 (pulse wave detecting sensor) provided to the end of cable 20. A wristband 12 is attached to device main body 10 which wraps around the user's wrist from the 12 o'clock position and affixes at the 6 o'clock position of the wristwatch. Device main body 10 can be freely attached and removed from the user's wrist by means of this wristband 12. Pulse wave detecting sensor unit 30 is blocked from light by band 40 employed for fixing the sensor in place, and is attached at the base of the user's index finger. By attaching pulse wave detecting sensor unit 30 in this way to the base of the finger, not only is cable 20 made shorter so that it does not present interference to the user during exercise, but the influence of the outside environment can also be reduced.

A-2: Structure of the Main Body of the Pulse Measurer

Figure 2:
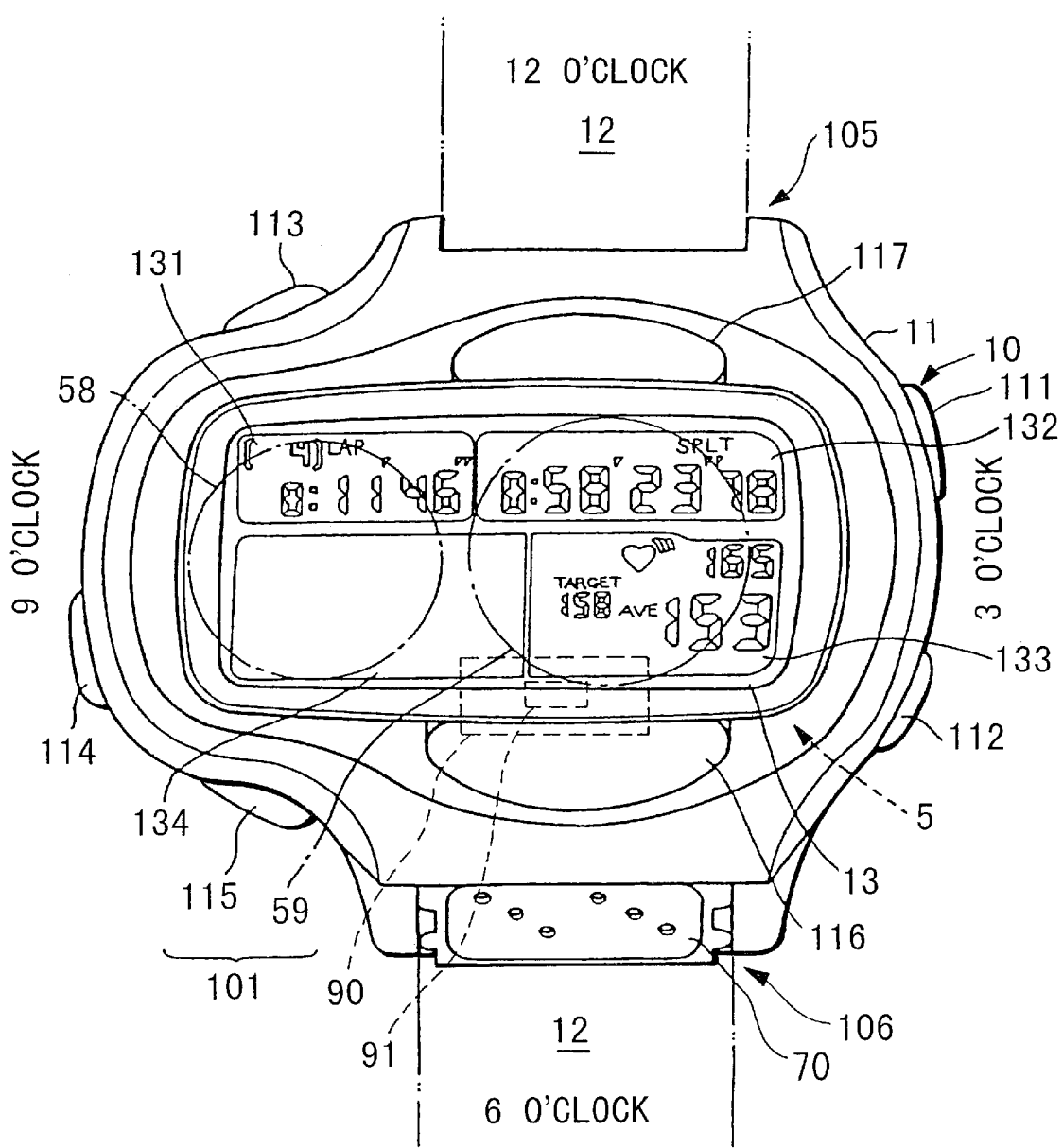
FIG. 2 is a planar view showing the state when the wristband or cable is released from the main body of the device in the same pulse measurer.
Figure 3:
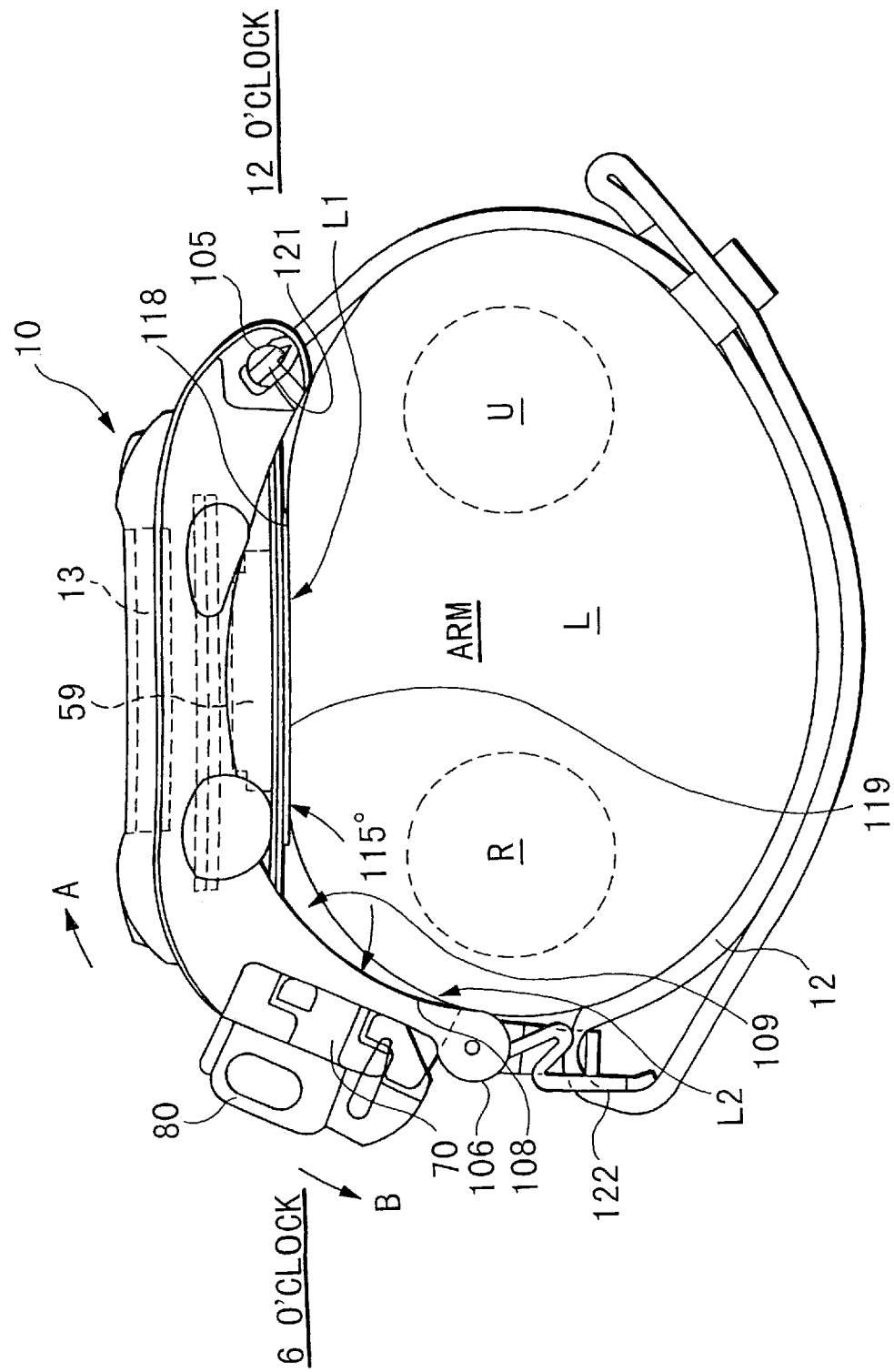
FIG. 3 is a side view of the same pulse measurer as seen from the 3 o'clock direction.

FIG. 2 is a planar view showing the state of the main body of the pulse measurer when the wristband or cable is released. FIG. 3 is side view showing the pulse measurer from the 3 o'clock direction. In FIG. 2, device main body 10 is provided with a watch case 11 (main body case) made of a resin. A liquid crystal display device 13 (display means) is provided to the surface of watch case 11 for displaying the current time and date, as well as the pulse rate and other pulse wave information. LCD device 13 is provided with first, second, and third segment display regions 131–133, respectively, and a dot display region 134. First segment display region 131 is positioned at the upper left area of the display panel; second segment display region 132 is positioned at the upper right area of the display panel; third segment display region 133 is positioned at the lower right area of the display panel; and dot display region 134 is positioned at the lower left area of the display panel. Graphic display of various information can be carried out on dot display region 134.

A controller 5 for carrying out control of the display device and signal processing on the detected signal is provided inside watch case 11, so that the display of changes in the pulse rate based on the results detected by pulse wave detecting sensor unit 30 can be displayed on LCD device 13. A watch circuit is formed in controller 5 so that the display of ordinary time, lap times or split times is possible on LCD device 13. Button switches 111~117 are provided to the outer periphery and surface of watch case 11, for carrying out external manipulations such as setting the time, switching the mode, or initiating measurement of lap time or pulse wave information.

The electrical source for a pulse measurer 1 of the type which attaches to the arm is a button-shaped battery 59 housed in watch case 11. Cable 20 supplies electric power from battery 59 to pulse wave detecting sensor unit 30, and inputs the results detected by sensor unit 30 to controller 5 in watch case 11. In order to ensure the wrist's freedom of movement and to protect the palm of the user's hand in the event of a fall, device main body 10 is enlarged in the 3 o'clock to 9 o'clock direction, with a large overhang 101 being further provided to the wristwatch in the 9 o'clock direction thereof. In addition, wristband 12 is connected at a position which is shifted toward the 3 o'clock side of the watch.

A flat piezo element 58 used as a buzzer (or used for producing informative sound) is disposed inside the watch case 11, at the 9 o'clock position with respect to the battery 59. Battery 59 is heavier than piezo element 58, such that the position of the center of gravity in the device main body 10 shifts toward the 3 o'clock side. Moreover, wrist band 12 is connected to the side of the main body 10 toward which the weight center has shifted. As a result, device main body 10 can be attached to the arm in a stable manner. Further, since battery 59 and piezo element 58 are disposed in the planar direction, device main body 10 may be made thinner. By providing a battery cover 118 to the rear surface 119 of the wrist watch, the user can easily change the battery 59.

A-3: Structure of Attachment of Pulse Measurer Main Body to Arm

In FIG. 3, a coupler 105 for holding a push pin 121 attached to the end of wristband 12 is formed at the 12 o'clock direction on watch case 11. At the 6 o'clock direction of watch case 11, wristband 12 wrapped around the arm is folded back at an intermediate point along its length, and a receiving member 106 to which stopper 122 attaches for holding at this intermediate position is formed.

At the 6 o'clock direction of device main body 10, a portion extending from the rear surface 119 to receiving member 106 forms a rotation stopping member 108 which is formed in a unitary manner with watch case 11 and forms an approximately 115° angle with rear surface 119. In other words, when device main body 10 is attached by means of wrist band 12 so as to be positioned on the supper surface L1 (on the palm side of the hand) of right wrist L (arm), then rear surface 119 of watch case 11 adheres to upper surface L1 of wrist L, while rotation stopping member 108 comes in contact with side surface L2 where the radius is present. In this arrangement, rear surface 119 of main body 10 straddles radius R and ulna U, while the portion extending from bent part 109 of rotation stopping member 108 and rear surface 119 to rotation stopping member 108 comes in contact with radius R. Because rotation stopping member 108 and rear surface 119 anatomically form a theoretical angle of about 115°, even if the user rotates device main body 10 in the direction of arrow A, or in the direction of arrow B, main body 10 does not deviate unnecessarily from its current state. In addition, since the rotation of device main body 10 is controlled by just two sites on either side of the arm through rear surface 119 and rotation stopping member 108, rear surface 119 and rotation stopping member 108 come in contact with the arm with surety even in the case of a thin arm. Thus, the effect of stopping rotation is obtained with certainty, while there is no pinching sensation even in the case of a thicker arm.

A-4: Structure of Pulse Wave Detecting Sensor Unit

Figure 4:
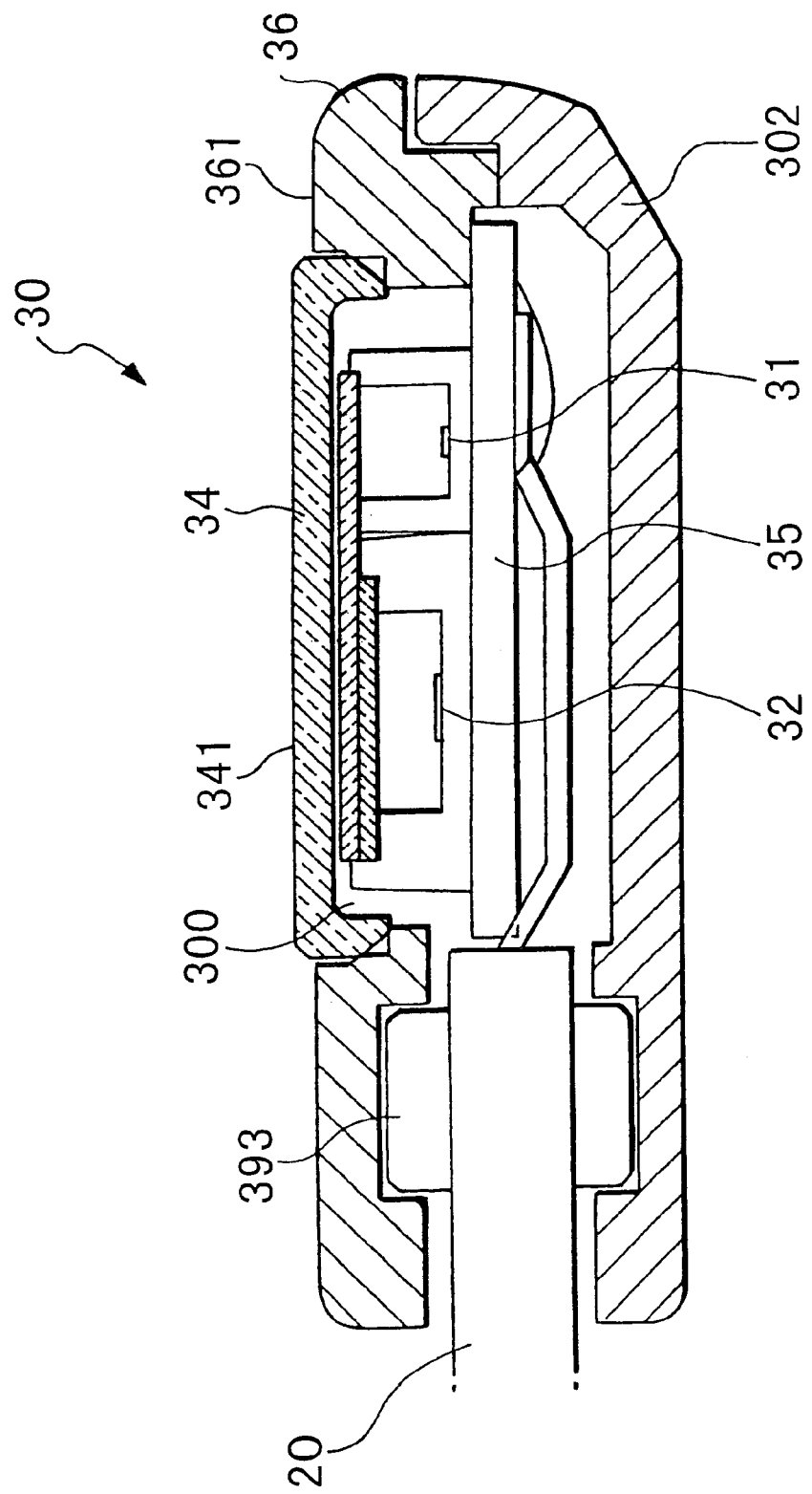
FIG. 4 is a cross-sectional view of pulse wave detecting sensor unit 30 of the same pulse measurer.

FIG. 4 is a cross-sectional view of the pulse wave detecting sensor unit in this embodiment. In the pulse wave detecting sensor unit 30 in FIG. 4, a component housing space 300 is formed therein by means of applying a cover 302 to the rear side of sensor frame 36 for the case body. Circuit board 35 is disposed inside this component housing space 300. LED 31, phototransistor 32, and other electronic parts are mounted on circuit board 35. The end of cable 20 is fixed in place at pulse wave detecting sensor unit 30 by a bush 393. Each of the wires of cable 20 are soldered onto the pattern of each of circuit boards 35. Pulse wave detecting sensor unit 30 is attached to the finger so that cable 20 is pulled out from the base of the finger to the side of device main body 10. Accordingly, LED 31 and photo transistor 32 are disposed so as to lie along the direction of the length of the finger. LED 31 is positioned on the side toward the tip of the finger, while photo transistor 32 is positioned at the base of the finger. As a result, light from the outside environment does not readily reach photo transistor 32.

In pulse wave detecting sensor unit 30, a light transmitting window is formed in the upper portion of sensor frame 36 (i.e., the area of actual pulse wave signal detection) by means of a light transmitting plate 34 consisting of a glass plate. The light emitting surface of LED 31 and the light receiving surface of photo transistor 32 are oriented in the direction of light transmitting plate 34. For this reason, when the surface of the finger adheres to the outer surface 341 (contact surface with finger surface/sensor surface) of light transmitting plate 34, LED 31 is positioned to emit light toward the finger surface, while photo transistor 32 is positioned to receive the light from LED 31 which has reflected off the surface of the finger. In order to improve the adherence between the outer surface 341 of light transmitting plate 34 and the surface of the finger, outer surface 341 of light transmitting plate 34 is formed so as to project out from the peripheral portion 361 thereof.

This embodiment employs a InGaN-type (indium-gallium-nitrogen) blue LED for LED 31. The generated light spectrum of a blue LED has a peak at 450 nm, for example, with the generated light wavelength region being in the range of 350 to 600 nm. In this case, a GaAsP-type (gallium-arsenic-phosphorous) photo transistor may be used for photo transistor 32 corresponding to LED 31 having the light emitting characteristics described above. The wavelength region of the received light of the photo transistor has, for example, a main sensitive region in the range of 300 to 600 nm, with a sensitive region also present below 300 nm.

A pulse wave detecting sensor unit 30 of this design is attached to the base of the finger using a sensor affixing pad 40. When, in this arrangement, light from LED 31 irradiates the finger, the light reaches the blood vessels where a portion thereof is absorbed by the hemoglobin in the blood. Light reflected from the finger (blood vessels) is received at photo transistor 32. Changes in the received light correspond to changes in the blood pressure (i.e., pulse waves in the blood). In other words, when the blood volume is great, there is weaker reflection of the light, while when the blood volume is small, there is stronger reflection of the light. Thus, it is possible to measure the pulse rate by detecting changes in the intensity of the reflected light.

This embodiment employed an LED 31 having a light generating region in the range of 350 to 600 nm, and a photo transistor 32 having a light receiving region in the range of 300 to 600 nm. Pulse wave information is expressed based on the results of detection in the overlapping wavelength region from 300 nm to 600 nm, i.e., in the wave length region that is below about 700 nm. If the above-described pulse wave detecting sensor unit 30 is employed, then, even if outside light strikes the exposed portion of the finger, light included in the outside light that is below 700 nm will not reach photo transistor 32 (receiving member) by employing the finger as a waveguide. Light in the wavelength region below 700 nm that is included in the outside light tends to have a difficult time passing through the finger, so that even if the portion of the finger not covered by sensor fixing pad 40 is irradiated with outside light, the light does not reach photo transistor 32 by passing through the finger as indicated by dashed line X. Moreover, the hemoglobin in blood has a large absorption coefficient with respect to light having a wavelength in the range of 300 nm to 700 nm, so that if light in a wavelength region of less than 700 nm is employed, it is possible to obtain a pulse wave signal having a high S/N ratio.

A-5: Structure of Connection Between Pulse Measurer Main Body and Pulse Wave Detecting Sensor Unit A connector 70 is provided at the 6 o'clock position to the surface of the portion of device main body 10 which extends as rotation stopping member 108. Connector piece 80, which is provided to an end of cable 20, is attached to connector 70 so as to be freely releasable. By releasing connector piece 80 from connector 70, pulse measurer 1 may be used as a regular wristwatch or stopwatch (in which case, a specific connector cover is attached to protect connector 70).

A-6: Structure of Controller

The structure of controller 5 of pulse measurer 1 will now be explained. However, since those parts relating to watch functions are well-known, an explanation thereof will be omitted, and only those parts relating to the pulse measuring functions will be explained here.

Figure 5:
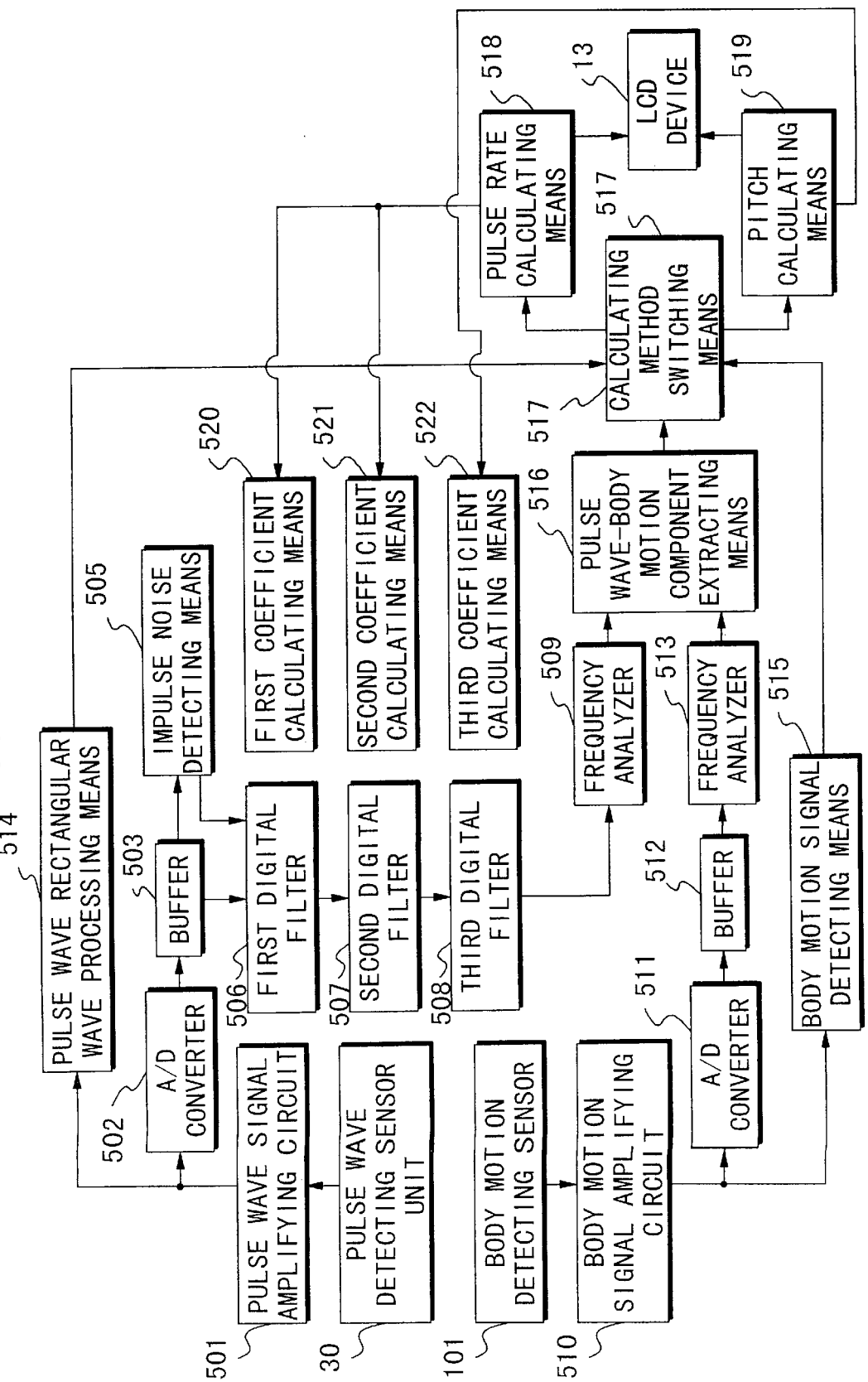
FIG. 5 is a block diagram showing the structure of the elements of controller 5 formed inside the main body of the same pulse measurer.

FIG. 5 is a block diagram showing the structure of the main parts of a controller 5 which is formed inside the main body of the pulse measurer. As shown in this figure, a body motion detecting sensor 101, such as an acceleration sensor or the like, is provided inside the main body of the pulse measurer. Controller 5 is provided with a design for determining the pulse rate and pitch of movement based on the results (body motion signal) detected by body motion detecting sensor 101 and the results (pulse wave signal) detected by pulse wave detecting sensor 30.

In controller 5, 501 is a pulse wave signal amplifying circuit for amplifying and outputting the detection results (pulse wave signal) from pulse wave detecting sensor unit 30; 502 is an A/D converter for converting the output (analog voltage signal) from pulse wave signal amplifying circuit 501 to a specific bit digital signal (−127~127, for example), and outputting this result; and 503 is a buffer for temporarily storing the output from A/D converter 502, and then outputting it. The capacity of buffer 503 is suitably set in correspondence with the duration of detection (for example, 16 seconds) during frequency analysis in the following step. Here, detection values corresponding to 4 seconds can be stored. Detected values corresponding to 4 seconds in buffer 503 are output immediately after the end of the processing to detect impulse noise, which will be discussed below. Thus, these 4 seconds have almost no effect on the device's overall delay time.

505 is an impulse noise detecting means. Impulse noise detecting means 505 determines whether or not the detected values that are stored in buffer 503 are being effected by impulse noise, and outputs the result of this determination. The method for making the aforementioned determination may be optionally selected. In this embodiment, a method is employed in which a "1" is output when the proportion of values detected outside a specific range with respect to the number of values detected overall in buffer 503 exceeds a specific threshold value, while a "0" is output in all other cases.

506~508 are first through third digital filters which sequentially carry out impulse noise removal processing, pseudo-window processing, and body movement component removal processing on the pulse wave signal output from buffer 503. A FIR filter is optimally employed for each of the digital filters, for example. The specifics of processing by each of the digital filters will be explained below. 509 is a frequency analyzer which performs frequency analysis (FFT processing, for example) on the pulse wave signal output from third digital filter 508, and outputs this result (spectrum). Although not shown in the figures, the pulse wave signal from digital filter 508 is provided with a recording means which is capable of recording a specific detection duration only (16 seconds, for example).

510 is a body motion signal amplifying circuit which amplifies the results (body motion signal) detected by body motion detecting sensor 101, and outputs this result. 511 is an A/D converter which converts the output (analog voltage signal) from body motion signal amplifying circuit 510 to a specific bit digital signal (−127~127, for example). 512 is a buffer for temporarily storing the output from A/D converter 511 and then outputting it. Buffer 512 has the same capacity as buffer 503.

513 is a frequency analyzer having the same structure as frequency analyzer 509. Frequency analyzer 513 carries out frequency analysis (FFT processing, for example) on the body motion signal output from buffer 512, and outputs this result (spectrum). Typically, the recording means for each of frequency analyzers 509 and 513 are provided in the same memory (RAM, for example).

514 is a pulse wave rectangular wave processing means which converts the pulse wave signal from the pulse wave signal amplifying circuit 501 to a rectangular wave, and outputs this result. 515 is a body motion signal detecting means which outputs the body motion detecting signal when the amplitude of the body motion signal from body motion signal amplifying circuit 510 exceeds a specific value (50 [mV] for example). 516 is a pulse wave-body motion component extracting means which extracts the frequency corresponding to the pulse and the frequency corresponding to the pitch of the body motion from the results output from each of frequency analyzers 509 and 513. 517 is a calculation method switching means for inputting the rectangular wave signal from pulse wave rectangular wave processing means 514 and each of the frequencies from pulse wave-body motion component extracting means 516, outputting a signal for calculating the pulse rate and the pitch, and then switching the signal output to the following step based on the body motion detection signal from body motion signal detecting means 515. An explanation of the processing for determining the frequency (frequency of the fundamental wave of body motion) with respect to the body motion pitch will be covered under the explanation of the device's operations.

When calculation method switching means 517 receives a body motion absent signal from body motion signal detecting means 515, it outputs to the following step the rectangular wave signal from pulse wave rectangular wave processing means 514 and the frequency corresponding to the pitch of body motion which was extracted by the pulse wave-body motion component extracting means 516, and stops the operation of A/D converter 502, buffer 503, impulse noise detecting means 505, first through third digital filters 506~508, and frequency analyzer 509. On the other hand, when calculation method switching means 517 receives a body motion present signal from body motion signal detecting means 515, it initiates operation of A/D converter 502, buffer 503, impulse noise detecting means 505, first through third digital filters 506~508, and frequency analyzer 509, and outputs each of the frequencies from pulse wave-body motion component extracting means 516 to the following step.

518 is a pulse rate calculating means which calculates the pulse rate based on the rectangular wave signal or frequency of the fundamental wave of the pulse wave supplied via calculation method switching means 517. 519 is a pitch calculating means for calculating the pitch of body motion based on the frequency of the fundamental wave of body motion supplied via calculation method switching means 517. Each of pulse rate calculating means 518 and pitch calculating means 519 supply the calculated pulse rate/pitch to LCD device 13. The calculation of the pulse rate/pitch from the frequency is realized by multiplying the frequency by the constant "60", while the calculation of the pulse rate/pitch from the rectangular wave signal is realized by measuring the period of the rectangular wave, and then multiplying the inverse of the measured value by the constant "60".

520 is a first coefficient calculating means (characteristics setting means) for calculating and outputting the coefficient set in first digital filter 506 based on the result (pulse rate) calculated by pulse rate calculating means 518. The characteristics of first digital filter 506 are expressed by the coefficient calculated by first coefficient calculating means 520 only when the result of the determination by impulse noise detecting means 505 is "1", i.e., only when impulse noise has been detected. In all other cases, the characteristics are such that all bands are through. The coefficient output by first coefficient calculating means 520 includes a frequency fb1 which becomes the reference (reference frequency), and cut-off frequencies f1, fh. Reference frequency fb1 is calculated based on the pulse rate detected immediately previously, while cut-off frequencies f1, fh are set in response to the change in the pulse rate. For example, if the change in the pulse rate is large and the stability of pulse transition is low, then cut-off frequencies f1, fh are set so that the interval with reference frequency fb1 becomes wider. Conversely, if the change in the pulse rate is small and the stability of pulse transition is high, then cut-off frequencies f1, fh are set so that the interval with reference frequency fb1 becomes more narrow. Note that an arrangement is also possible in which cut-off frequencies f1, fh are set so that the interval with reference frequency fb1 becomes constant.

An example of the characteristics of the first digital filter which is specified by the coefficient value output by first coefficient calculating means 520 is shown in FIG. 6(*a*). As shown in this figure, the characteristics which are set in first digital filter 506 when impulse noise is detected by impulse detecting means 505 form a hill-shaped curve, the highest point of which is the level at which reference frequency fb1 passes through the filter. Namely, the damping factor of the signal input to first digital filter 506 falls in the vicinity of reference frequency fb1 in the frequency domain. As the distance from reference frequency fb1 increases, the damping factor increases, until it exceeds cut-off frequency f1, fh beyond some given distance, and the signal is cut-off.

In this embodiment, when the reference frequency fb1 is 2.3 [Hz], i.e., when the pulse rate through the immediately preceding point in time is 140 [beats/sec], the value output from first digital filter 506 at the time of detection of impulse noise is set so as to be the weighted average value of 5 sampling points:

$$X_N = (-1 \cdot X_N - 1 \cdot X_{N+1} + 4 \cdot X_{N+2} - 1 \cdot X_{N+3} - 1 \cdot X_{N+4})/8$$

(N=0,1,2,3,4, . . . ,N−1)

521 is a second coefficient calculating means which calculates the coefficient set in second digital filter 507 based on the results (pulse rate) calculated at pulse rate calculating means 518, and outputs this result. Without exception, the characteristics of second digital filter 507 are the characteristics expressed by the coefficient calculated at second coefficient calculating means 521. An example of the characteristics of second digital filter 507 which is specified by the coefficient output from second coefficient calculating means 521 is shown in FIG. 6(*b*). As shown in this figure, the characteristics set in second digital filter 507 form a hill-shaped curve in which the damping factor of fundamental frequency fb1 is lowest and then gradually increases toward the base of the hill.

Second coefficient calculating means 521 is provided with a recording means for recording only a specific number of the most recent pulse rates. Second coefficient calculating means 521 supplies the coefficient in response to the change in the pulse rate that is recorded in the recording means to second digital filter 507, and changes the slope of the edge line of the characteristics. For example, when the change in the pulse rate is small, the slope of the edge line is sharp, while when the change is large, the slope of the edge line is more gradual. As a result of this design, it is possible to avoid the situation in which the pulse wave components in the pulse wave signal fall sharply, while also decreasing non-pulse wave noise components.

522 is a third coefficient calculating means (means for setting characteristics of the filter) which calculates the coefficient set in the third digital filter 508 based on the results (pitch) calculated at pitch calculating means 519, and outputs this result. Without exception, the characteristics of third digital filter 508 are the characteristics expressed by the coefficient calculated at third coefficient calculating means 522. An example of the characteristics of third digital filter 508 which is specified by the coefficient value output from third coefficient calculating means 522 is shown in FIG. 6(*c*). As shown in this figure, the characteristics set in third digital filter 508 are pinched at frequencies which are multiples of the fundamental frequency fb2 (frequency of the fundamental wave of body motion), i.e., cut-off the components of frequencies which are multiples of the fundamental frequency fb2 (body motion component).

Third coefficient calculating means 522 is provided with a recording means for recording only a specific number of the most recent pitches. Third coefficient calculating means 522 supplies the coefficient in response to the change in the pitch that is recorded in the recording means to third digital filter 508, and changes the strength of the pinching. For example, when the change in the pitch is small, the pinching is made stronger and the components of frequencies which are multiples of fundamental frequency fb2 are greatly damped. Conversely, when the change is large, the pinching is made small, and there is not very much damping even if there are components of frequencies which are multiples of the fundamental frequency fb2. As a result of this design, it is possible to avoid the situation in which the pulse wave components in the pulse wave signal fall sharply, while also greatly decreasing non-pulse wave noise components (body motion components).

Note that in this embodiment, LCD device 13 carries out the numerical display of the pulse rate and pitch in specific regions. However, it is also acceptable to display pictorial characters corresponding to numerical values, or graphs showing the state of pulse rate and pitch changes. A sweep display is also acceptable for the wave form (pulse waveform) expressed by the pulse wave signal output from third digital filter 508.

The structural elements which were functionally expressed in the preceding explanation are realized as software by means of circuit elements like a CPU, ROM, RAM or the like. The method for realizing these structural elements is voluntary matter of design. Accordingly, an explanation is omitted as to which structural element is realized with which circuit element. Finally, from the perspective of saving space and lowering costs, a design is desirable in which as much as possible the above-described circuit elements serve in both the watch mode and the pulse measurer mode.

B: OPERATION OF THE EMBODIMENT

The operation of the above-described embodiment will now be explained. However, since the operation of this device as a watch is well-known, an explanation of this function will be omitted here. Note that switching between the watch mode and the pulse measurer mode can be accomplished by depression of a specific button.

B-1: Calculation Method Switching Operation

Figure 7:
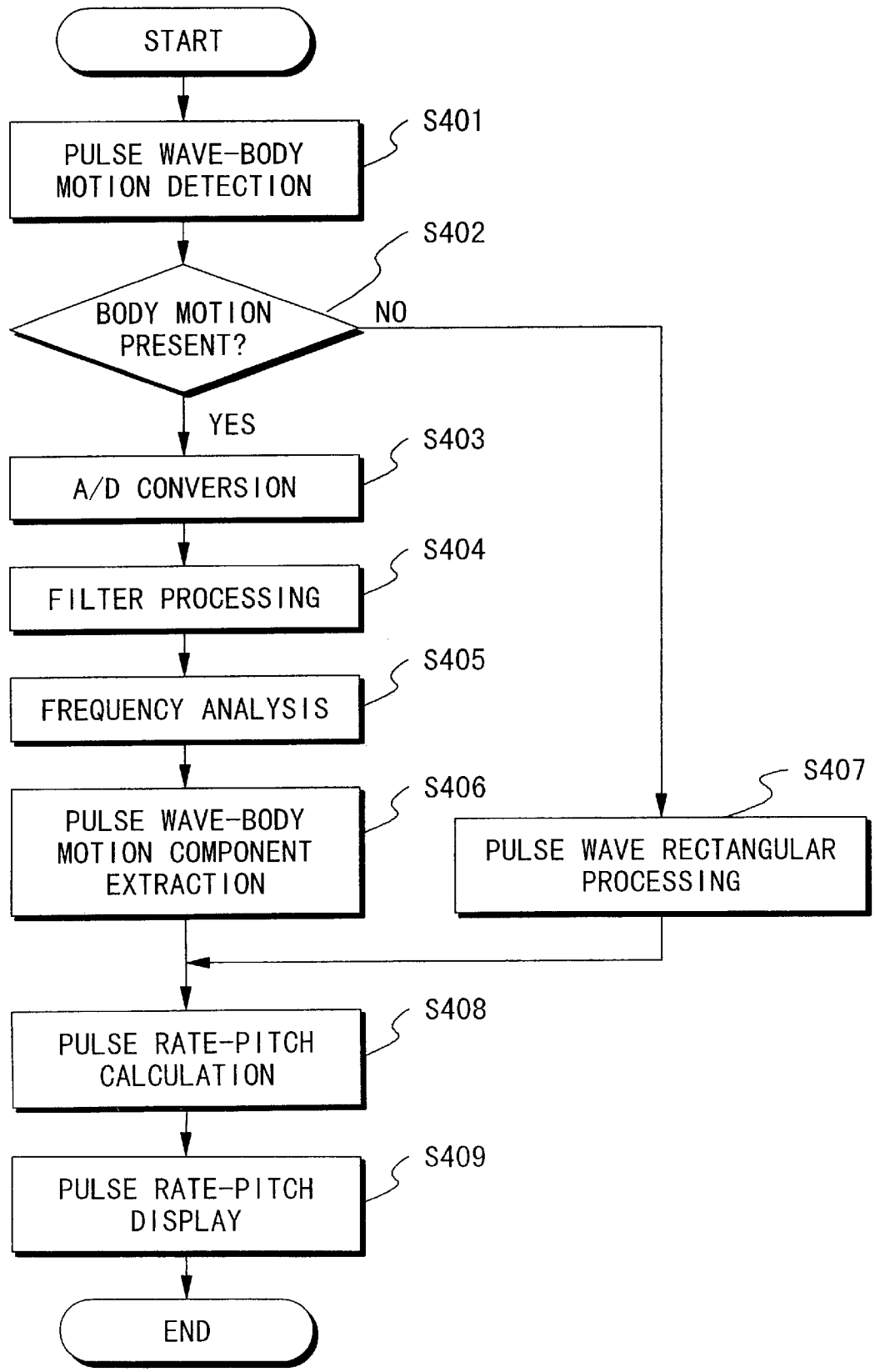
FIG. 7 is a flow chart showing the flow of basic processing in the same pulse measurer.

FIG. 7 is a flow chart showing the flow of basic processing in the pulse measurer mode. As shown in this figure, in the pulse measurer mode, pulse wave detecting sensor unit 30 and body motion detecting sensor 101 ordinarily output a pulse wave signal and a body motion signal. The body motion signal output from body motion detecting sensor 101 is amplified by body motion signal amplifying circuit 510, and supplied to body motion signal detecting means 515. As a result, the body motion detecting signal which serves as the reference for switching the pulse rate calculation method is supplied to calculation method switching means 517 from body motion signal detecting means 515. In calculation method switching means 517, the method for calculating the pulse rate (i.e., frequency analysis method/rectangular wave processing method) is switched based on the body motion detection signal supplied from the body motion signal detecting means 515 (steps S401, S402).

Specifically, when a body motion detection signal is supplied from body motion signal detecting means 515, and when the time period during which a body motion detection signal is not supplied is less than a specific period of time, then a "body motion present" determination is made. The output from pulse wave-body motion component extracting means 516 is supplied without alteration to pulse rate calculating means 518 and pitch calculating means 519 which are the subsequent steps. As a result, the calculation method is switched to the frequency analysis method. Conversely, when the time period during which a body motion detection signal is not supplied exceeds a specific period of time, then a "body motion absent" determination is made. A rectangular wave signal from pulse wave rectangular wave processing means 514 and the frequency with respect to the body motion pitch from pulse wave-body motion component extracting means 516 are supplied to pulse rate calculating means 518 and pitch calculating means 519. As a result, the calculation method is switched to the rectangular wave processing method. Additionally, in order to conserve energy, the operations of unnecessary circuit elements, or the power supply to these elements, is suspended in each of these methods.

B-2: Rectangular Wave Processing Method

When the rectangular wave processing method is employed as the calculation method, the pulse wave signal detected by pulse wave detecting sensor unit 30 is amplified by pulse wave signal amplifying circuit 501, converted to a rectangular wave signal by pulse wave rectangular wave processing means 514, and supplied to pulse rate calculating means 518 via calculation method switching means 517. On the other hand, the body motion signal detected by body motion detecting sensor 101 is amplified by body motion signal amplifying circuit 510, converted to a digital signal at A/D converter 511, and stored temporarily in buffer 512. The body motion signal output from buffer 512 is subjected to frequency analysis processing (for example, FFT processing in which the duration of detection is 16 seconds) at frequency analyzer 522, and the frequency of the fundamental wave of body motion is extracted by pulse wave-body motion component extracting means 516 from the results of this frequency analysis.

The processing by which pulse wave-body motion component extracting means 516 determines the frequency of the fundamental wave of body motion and the pulse wave from each of the frequency analysis results (spectrums) described above will now be explained with reference to FIG. 8.

FIG. 8 shows an example of the results obtained from frequency analysis of the body motion signal. In general, as shown in this figure, the level of the frequency component of the second harmonic of body motion is higher than the frequency component of the fundamental wave of body motion (i.e., the fundamental wave of the user's arm movements). This is due to the following. Namely, the fundamental wave of body motion corresponds to a pendulum motion, in which the swinging forward and drawing back motion of the arms constitutes one period. Typically, however, it is difficult to render the swinging of the arms during running into a smooth pendulum motion, so that the level of this component is low. In contrast, the second harmonic of body motion corresponds to the vertical movement generated uniformly when taking steps with the right and left feet, and to the acceleration that is applied at the instant the arms swing forward and the instant they are drawn back. Thus, second harmonic components appear at a high level.

Accordingly, the second harmonic components of body motion are characteristically easy to obtain. In the case of ordinary running, given a range of 2 to 4 Hz, it is possible to cover the region in which the second harmonic appears, regardless of whether the pace of running is slow or fast. Accordingly, by extracting the characteristic second harmonic component after limiting the region in this way, it is possible to achieve a higher accuracy of detection.

Therefore, in this embodiment, the frequency (fs) of the highest level spectral line is determined from the results of frequency analysis of the body motion signal. A determination is then made as to whether or not a spectral line above a specific threshold level is present in the frequency domain which is ½ that of fs. When a determination is made that such a spectral line is present, fs is designated as the frequency of the second harmonic of body motion, and fs/2 is designated as the frequency of the fundamental wave of body motion. When a determination is made that a spectral line having a level above a given threshold value is not present, then fs is assumed to be the frequency of the third harmonic, and a determination is made as to whether or not a spectral line of a level above a given threshold value is present in the fs/3 frequency domain. If such a spectral line is found to be present, then fs/3 is specified as the frequency of the fundamental wave of body motion, while if such a spectral line is found to be absent, fs is specified as the frequency of the fundamental wave of body motion. Note that the reason why consideration is given through the third harmonic is that a range of 2~4 [Hz] has been assumed for the range in which the fundamental wave of body motion can be found to be present.

The frequency of the fundamental wave of body motion thus specified is supplied to pitch calculating means 519 via calculation method switching means 517. The preceding is the processing in step S407 in FIG. 7.

The period (value of the wave interval) of the rectangular wave signal supplied via pulse wave-body motion component extracting means 516 is obtained in pulse rate calculating means 518. The value obtained by multiplying the reciprocal of the period (i.e., the frequency) by 60 is designated as the pulse rate. In pitch calculating means 519, the value obtained by multiplying the frequency supplied via pulse wave-body motion component extracting means 516 by 60 is designated as the pitch (step S408). Calculating means 518 is designed to supply the calculated pulse rate to coefficient calculating means 520,521, and calculating means 519 is designed to supply the calculated pitch to coefficient calculating means 522. However, the processing to supply the calculated pulse rate and pitch is halted during the time period that the rectangular wave processing method has been selected (of course, an arrangement is also possible in which supply processing is carried out in both cases). The pulse rate and pitch calculated by calculating means 518 and 519 are displayed by supplying them to LCD device 13, thereby providing visual notification to the user (step S409). An arrangement is also possible in which the notification is provided to the user be a means which does not rely on visual senses, such as using a tone to alert the user of the pulse rate and pitch.

B-3: Frequency Analysis Method

When the frequency analysis method is employed as the calculation method, the pulse wave signal detected by pulse wave detecting sensor unit 30 is amplified by pulse wave signal amplifying circuit 501, converted to a digital signal (for example, an integer value in the range of –127~127) by A/D converter 502 (step S403), and temporarily stored in buffer 503. Since the processing carried out on the body motion signal to obtain the frequency of the fundamental wave of body motion is equivalent to that described under the preceding section "B-2: Rectangular wave process method", an explanation thereof is omitted here.

Filter processing by first through third digital filters 506~508 is carried out on the pulse wave signal that was temporarily stored in buffer 503, thereby reducing or removing the noise component in the pulse wave signal (step S404). This filter processing will now be explained in order below.

When the detected value (a 4-second pulse wave signal, for example) stored in buffer 503 is not being effected by impulse noise, i.e., more specifically, when the proportion of values detected outside a specific range with respect to the number of values detected overall in buffer 503 is below a specific threshold value, then a signal (a signal which a value of "0", for example) indicating that impulse noise was not detected is output from impulse noise detecting means 505 according to the timing at which the detected value is output from buffer 503 to first digital filter 506. The coefficient calculated by first coefficient calculating means 520 based on the pulse rate calculated immediately previously is supplied to first digital filter 506. Because a signal indicating that impulse noise was not detected is supplied from impulse noise detecting means 505, those characteristics pass through for all bands. Accordingly, the pulse wave signal is supplied without modification to second digital filter 507.

Figure 6A:
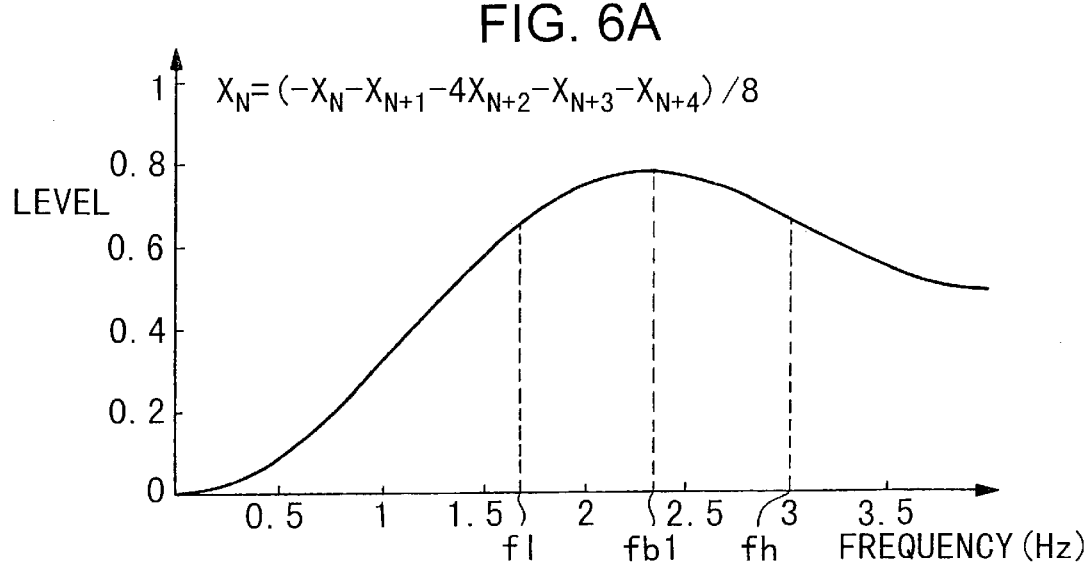
FIG. 6 shows examples of the characteristics of the digital filter in the same pulse measurer, wherein (a) shows the characteristics of the first digital filter, (b) shows the characteristics of the second digital filter, and (c) shows the characteristics of the third digital filter.

In contrast, when the detected value stored in buffer 503 is being effected by impulse noise, i.e., more specifically, when the proportion of values detected outside a specific range with respect to the number of values detected overall in buffer 503 exceeds a specific threshold value, then a signal (a signal having a value of "1", for example) indicating that impulse noise was detected is output from impulse noise detecting means 505 according to the timing at which the detected value is output from buffer 503 to first digital filter 506. In this case, the characteristics of first digital filter 506 become such as shown in FIG. 6(a), and components which are not frequency components of the anticipated pulse wave are damped or cut-off.

Figure 9A:
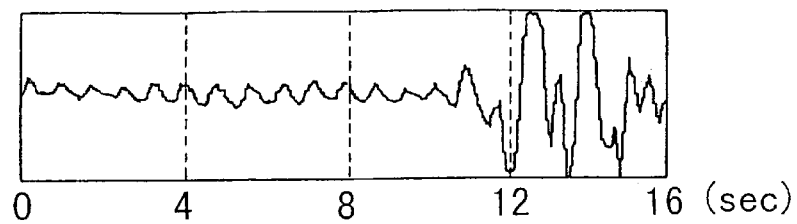
FIG. 9(a) shows an example of the waveform of the pulse wave signal before filter processing by the first digital filer in the same pulse measurer.
Figure 9B:
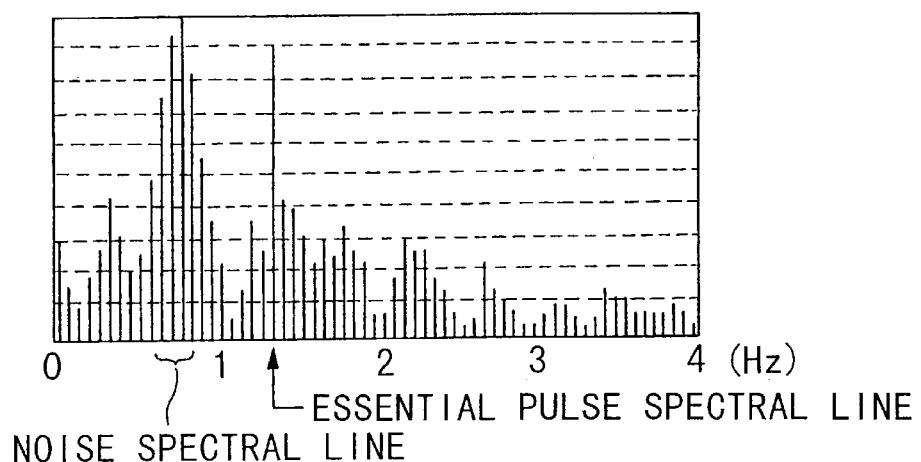
FIG. 9(b) shows the result obtained after FFT processing of the waveform in FIG. 9(a).
Figure 10A:
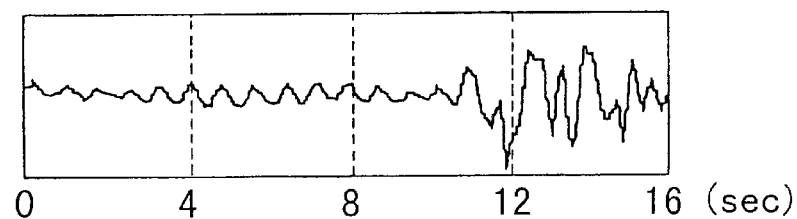
FIG. 10(a) shows an example of the waveform of the pulse wave signal after the signal in FIG. 9(a) has been subjected to filter processing by the first digital filter.
Figure 10B:
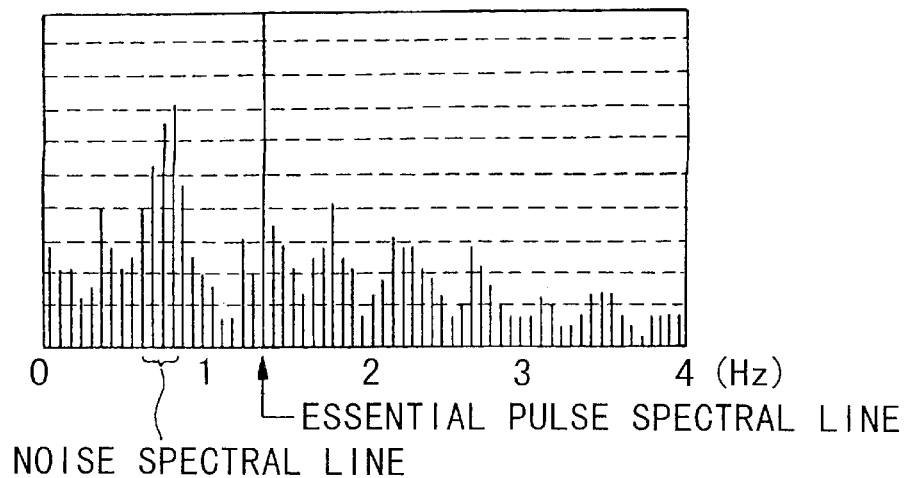
FIG. 10(b) shows the result obtained by FFT processing of the waveform in FIG. 10(a).
Figure 11A:
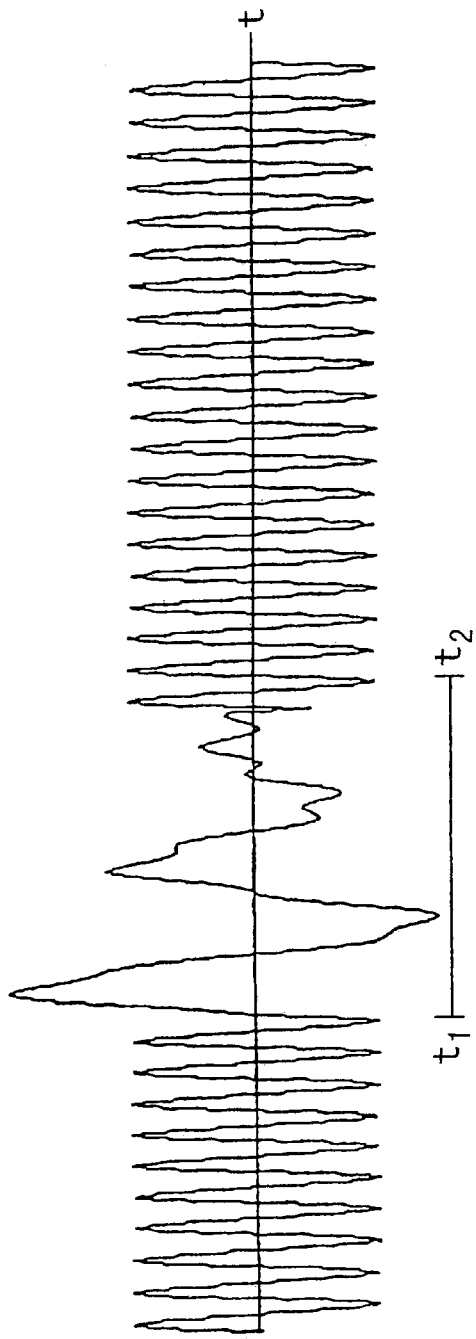
Figure 11B:
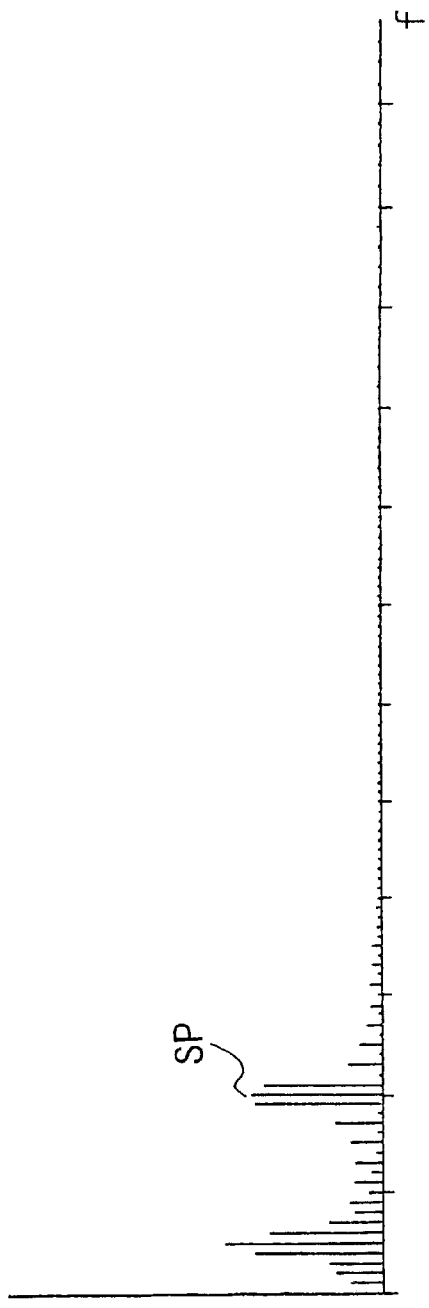
FIG. 11(b) shows the spectrum obtained after performing FFT on the pulse wave signal in FIG. 11(a).
Figure 13:
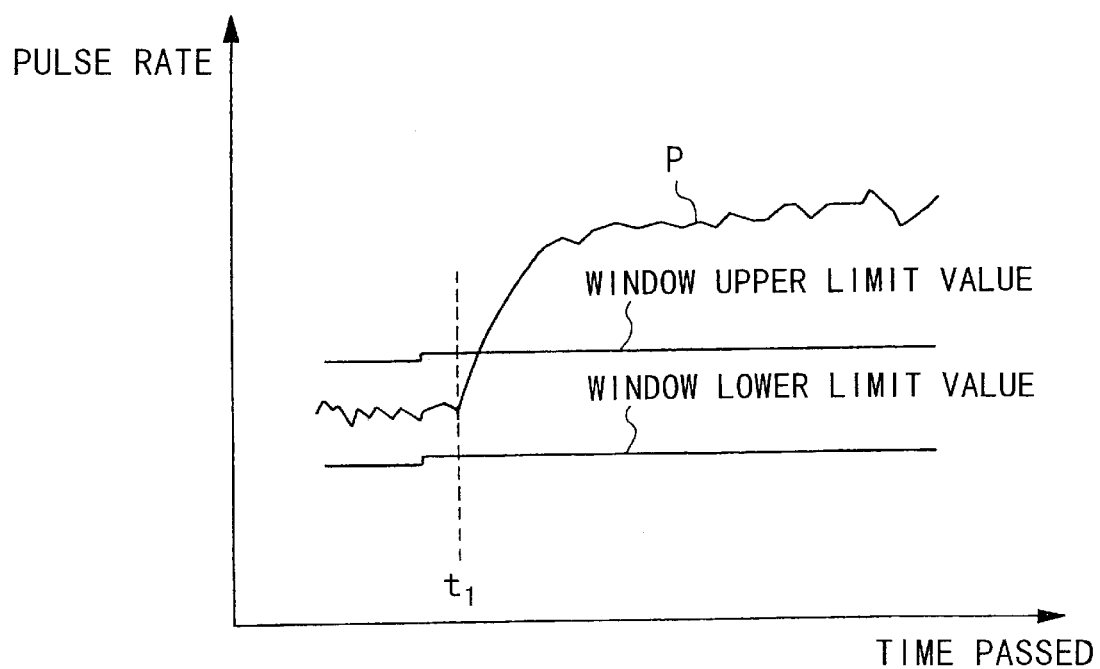
FIG. 13 is a figure for explaining conventional window processing.
Figure 14A:
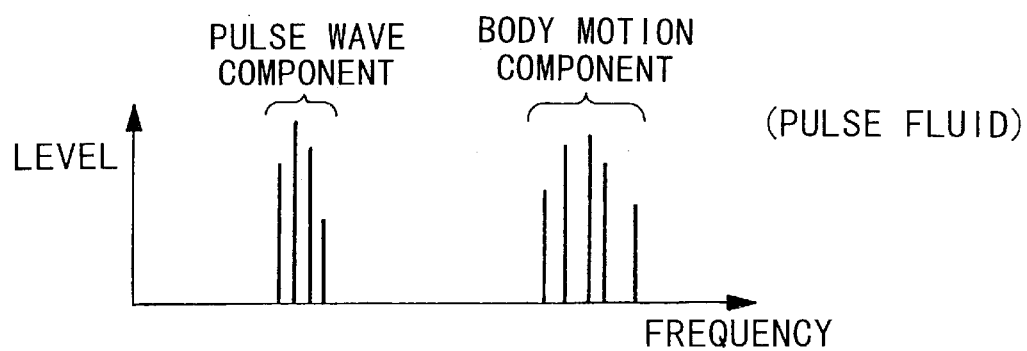
Figure 14B:
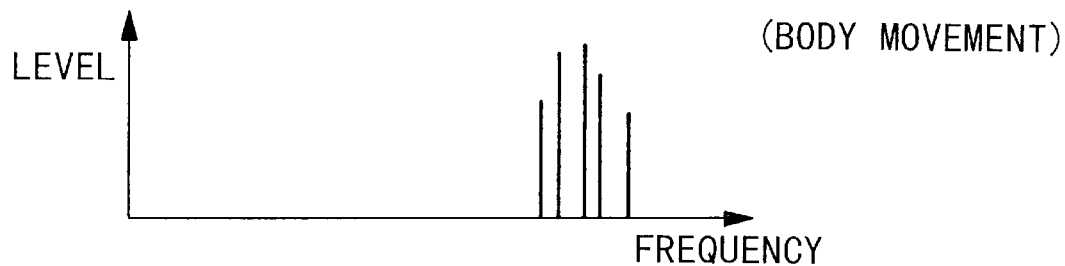
FIG. 14(b) shows the spectrum obtained after performing FFT processing on the body motion signal.
Figure 14C:
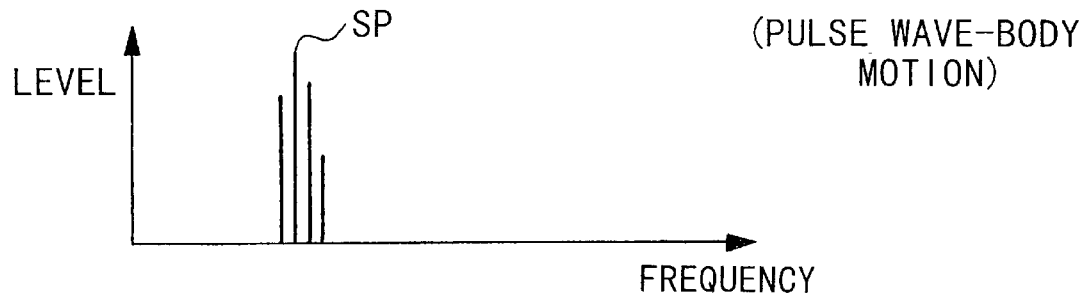
FIG. 14(c) shows the spectrum which is the result of subtracting the spectrum in FIG. 14(b) from the spectrum in FIG. 14(a).

An example of the waveform of the pulse wave signal before filtering by first digital filter 506 is shown in FIG. 9(a), while the result obtained after FFT processing of this waveform is shown in FIG. 9(b). An example of the waveform of the pulse wave signal after filtering of this same pulse wave signal by first digital filter 506 is shown in FIG. 10(a), while the result obtained after FFT processing of this waveform is shown in FIG. 10(b). As shown in these figures, low frequency components (impulse noise) are greatly damped by first digital filter 506. Namely, the impulse noise component in the pulse wave signal is greatly reduced or removed by first digital filter 506.

Figure 6B:
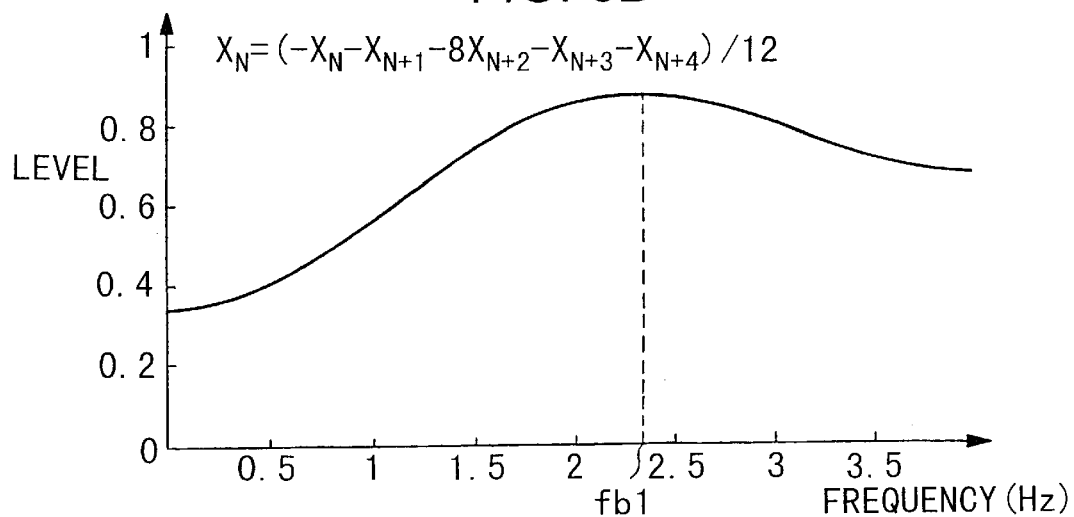

The coefficient calculated by second coefficient calculating means 521 based on the pulse rate calculated immediately previously is supplied to second digital filter 507. These characteristics are as shown in FIG. 6(b). In other words, these characteristics are such that the degree of damping increases with greater distance from the frequency of the pulse wave. Accordingly, in addition to impulse noise, other noise components are also damped. In situations in which the pulse rate does not change abruptly, such as when the user is at rest, then a frequency component which is only slightly separated from the frequency of the anticipated pulse wave may also be considered a noise component.

In situations when the pulse changes abruptly, such as at the start of exercise, there is a possibility that frequencies that are separated to some degree from the frequency of the pulse wave anticipated will include essential pulse wave components. Therefore, second coefficient calculating means 521 is designed to make the slope of the edge line in FIG. 6(b) steep when the change in the pulse rate is small, and to make the slope more gradual when the change in the pulse rate is large, so that noise components are damped without damping the essential pulse wave components very much.

Figure 6C:
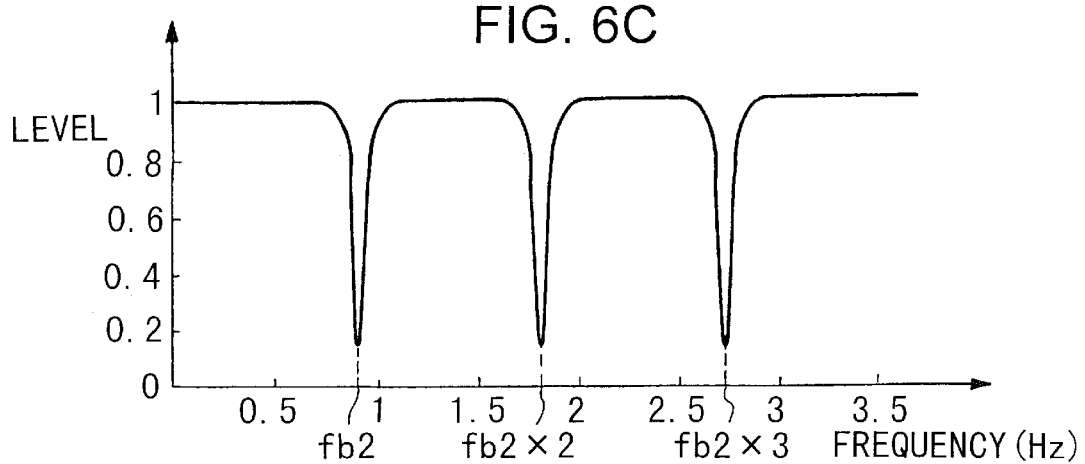

The coefficient calculated by third coefficient calculating means 522 based on the pitch calculated immediately previously is supplied to third digital filter 508, with these characteristics being as shown in FIG. 6(c). As explained above, reference frequency fb2 is the frequency of the fundamental wave of body motion. Accordingly, the harmonic components and the fundamental wave component of body motion in the pulse wave signal are damped. Additionally, in the same way that second coefficient calculating means 521 acts on second digital filter 507, third coefficient calculating means 522 intensifies the pinching in FIG. 6(c) when the change in the pitch is small and reduces the pinching when the change in the pitch is large. Accordingly, in situations where the pitch does not change abruptly, the body motion components are greatly reduced or removed, while in situations when the pitch does change abruptly, such as when exercise is initiated, the preceding pitch and the current pitch may differ greatly. Thus, damping of the body motion components is confined to a small amount.

The pulse wave signal thus shaped is subjected to specific frequency analysis processing (in this embodiment, FFT processing having a detection time of 16 seconds) by frequency analyzer 509 (step S405).

Next, pulse wave-body motion component extracting means 516 specifies the frequency of the fundamental wave of body motion and the pulse wave from the results (spectrums) obtained from the above-described frequency analysis (step S406). The processing for determining the frequency of the fundamental wave of the pulse wave will now be explained.

Pulse wave-body motion component extracting means 516 first selects the spectral lines in order starting with the highest level spectral line from among the results obtained from frequency analysis of the pulse wave signal. Pulse wave-body motion component extracting means 516 then compares the frequency of the selected spectral lines with the frequency of the fundamental wave of body motion (fs/2 for example) and the frequency of the higher harmonic waves (fs, 3 fs/2, for example). If they do not coincide, pulse wave-body motion component extracting means 516 specifies the frequency of the aforementioned spectral lines as the frequency of the fundamental wave of the pulse wave. The frequency of the fundamental wave of the pulse wave thus specified is then supplied to pulse rate calculating means 518 via calculation method switching means 517.

The fundamental wave and harmonic components of body motion are greatly reduced or removed from the pulse wave signal by third digital filter 509. Accordingly, it is theoretically acceptable to provide a design in which the frequency of the highest level spectral line from the results of frequency analysis of the pulse wave signal is simply specified as the frequency of the fundamental wave of the pulse wave. However, in this case, when the pitch changes abruptly, the amount of damping carried out on the fundamental wave and harmonic components of body motion by the third digital filter remains slight. Thus, there is a possibility that the spectral lines of the remaining body motion components may be selected as the spectral line of the fundamental wave of the pulse wave. Accordingly, it is preferable to change the processing in response to the degree of change in the pitch.

Next, the pulse rate is calculated from the aforementioned frequency at pulse rate calculating means 518 to which the frequency of the fundamental wave of the pulse wave is supplied. This pulse rate is supplied to LCD device 13, first coefficient calculating means 520, and second coefficient calculating means 521. The pitch is calculated from the frequency at pitch calculating means 519 to which the frequency of the fundamental wave of body motion was supplied. This pitch is supplied to LCD device 13 and third coefficient calculating means 522 (step S408). It is also acceptable to provide a design in which the value supplied from pulse rate calculating means 518 to first coefficient calculating means 520 and second coefficient calculating means 521, and the value supplied from pitch calculating means 519 to third coefficient calculating means 522, are designated as each of the frequencies supplied via calculation method switching means 517, and in which each of coefficient calculating means 520~522 calculate the coefficients based on each of the aforementioned frequencies.

Note that the pulse rate and pitch supplied to LCD device 13 are displayed in the corresponding region, thereby providing notice to the user (step S409).

C: SUMMARY

As explained above, the present embodiment enables damping or removal of noise components in a pulse wave signal by employing first through third digital filters 506~508. As a result, it is possible to improve the accuracy of processing to detect the pulse rate using frequency analysis in a subsequent step. In addition, the pulse wave signal itself is shaped, so that, for example, in an arrangement in which the pulse wave itself is displayed, it is possible to display an even more accurate waveform for the pulse wave.

Moreover, at the first digital filter, when impulse noise has not been generated, then the signal over the entire region passes through the filter. Thus, pulse wave signals which do not contain superimposed impulse noise are not subjected to filtering. Further, since filtering primarily damps or removes impulse noise components, there is no concern that essential pulse wave components present in the area of superimposition of the impulse noise will be greatly reduced or removed.

Since frequency components to be removed are not present, or at least have been damped, at the second digital filter, there is no concern that essential pulse wave components will be removed, even if the pulse rate changes abruptly. The frequency components of the fundamental wave and higher harmonic waves of body motion are greatly damped or removed at the third digital filter, thus subsequent processing is reduced. In addition, since the characteristics of the second and third digital filters can be changed in response to the degree of change in the pulse rate or pitch, it is possible to obtain an even more accurate pulse waveform and pulse rate.

D: MODIFICATIONS

The preceding embodiments employed first~third digital filters simultaneously, however an arrangement is also possible in which only one or two of these filters is employed. It is also acceptable to combine the second and third digital filters to realize a single filter. An arrangement may also be considered in which the buffer and impulse noise detecting means are omitted, and filtering is carried out on all pulse wave signals using the first digital filter. In this case, first through third digital filters may be realized as one single filter. In addition, the arrangement for mounting the device is not limited to a wristwatch, rather, a necklace or eyeglasses may also be considered. Of course, the pulse measurer may also be used alone, or as a device for detecting pulse waves.

What is claimed:

1. A pulse wave detecting device comprising:
    a pulse wave detecting sensor for detecting pulse waves and outputting pulse wave signals;
    a filter having variable characteristics for filtering the pulse wave signal output from said pulse wave detecting sensor and outputting the result, and being capable of changing said characteristics including distribution characteristics of pass levels for a pass band of the filter;
    a pulse rate calculating means for calculating the pulse rate based on the pulse wave signal which was filtered by said filter; and
    a characteristics setting means for setting characteristics of said filter based on the pulse rate calculated by said pulse rate calculating means.

2. A pulse wave detecting device according to claim 1, further comprising:
    a buffer for temporarily storing the pulse wave signal output from said pulse wave sensor and then outputting it to said filter; and
    an impulse noise detecting means for detecting impulse noise from the pulse wave signal that was temporarily stored in said buffer;

wherein, said characteristics setting means sets the characteristics of said filter after taking into account the results of detection by said impulse noise detecting means.

3. A pulse wave detecting device according to claim 1, wherein:

said filter is constructed so that a level at which the pulse wave signal passes through said filter gradually becomes lower from a reference frequency to the lower and upper limit frequencies of the fundamental wave of the pulse wave; and said characteristics setting means sets characteristics of said filter by setting the reference frequency.

4. A pulse wave detecting device according to claim 1, wherein said characteristics setting means changes the characteristics set in said filter in response to the state of change in the pulse rate calculated by said pulse rate calculating means.

5. A pulse measurer having the pulse wave detecting device according to claim 1, further comprising a notifying means for notifying a user of the pulse rate calculated by said pulse rate calculating means.

6. A pulse wave detecting device comprising:

a pulse wave detecting sensor for detecting the pulse wave and outputting pulse wave signals;

a filter having variable characteristics for filtering the pulse wave signal output from said pulse wave detecting sensor and outputting the result;

a body motion detecting sensor for detecting body motion and outputting a body motion signal;

a pitch calculating means for calculating a pitch of the body motion based on the body motion signal output from said body motion detecting sensor; and a characteristics setting means for setting characteristics of said filter based on the pitch calculated by said pitch calculating means.

7. A pulse wave detecting device according to claim 6 wherein said characteristics setting means changes the characteristics set in said filter in response to the state of change in the pitch calculated by said pitch calculating means.

8. A pulse measurer having the pulse wave detecting device according to claim 2, further comprising a pulse rate calculating means for calculating the pulse rate based on the pulse wave signal that was filtered by said filter, and a notifying means for notifying a user of the pulse rate calculated by said pulse rate calculating means.

9. A pulse wave detecting device comprising:

a pulse wave detecting sensor for detecting pulse waves and outputting pulse wave signals;

a filter having at least three kinds of characteristics for filtering the pulse wave signal output from said pulse wave detecting sensor and outputting the result;

a pulse rate calculating means for calculating a pulse rate based on the pulse wave signal filtered; and a characteristics setting means for setting characteristics of said filter based on the pulse rate calculated by said pulse rate calculating means.

10. A pulse wave detecting device comprising:

a pulse wave detecting sensor for detecting pulse waves and outputting pulse wave signals;

an analog-to-digital converter for converting the pulse wave signal output from said pulse wave detecting sensor;

a filter having variable characteristics for filtering the pulse wave signal converted by said analog-to-digital converter and outputting the result;

a pulse rate calculating means for calculating a pulse rate based on the pulse wave signal filtered; and a characteristics setting means for setting characteristics of said filter based on the pulse rate calculated by said pulse rate calculating means.

11. A pulse wave detecting device comprising:

a pulse wave detecting sensor for detecting pulse waves and outputting pulse wave signals;

a filter having variable characteristics for filtering the pulse wave signal output from said pulse wave detecting sensor and outputting the result;

a frequency analyzer for analyzing the filtered pulse wave signal;

a pulse rate calculating means for calculating a pulse rate based on a result from the frequency analyzer; and a characteristics setting means for setting characteristics of said filter based on the pulse rate calculated by said pulse rate calculating means.

12. A pulse wave detecting device comprising:

a pulse wave detecting sensor for detecting pulse waves and outputting pulse wave signals;

a buffer for temporarily storing the pulse wave signal output from said pulse wave sensor;

a filter having variable characteristics for filtering the pulse wave signal from said pulse wave detecting sensor and outputting the result;

a pulse rate calculating means for calculating a pulse rate based on the filtered pulse wave signal;

an impulse noise detecting means for detecting non-routine impulse noise from the pulse wave signal temporarily stored in said buffer; and a characteristics setting means for setting characteristics of said filter based on a pitch calculated by a pitch calculating means and the non-routine impulse noise detected by said impulse noise detecting means.

13. A pulse wave detecting device comprising:

a pulse wave detecting sensor for detecting pulse waves and outputting pulse wave signals;

a filter having variable characteristics for filtering the pulse wave signal, wherein said filter is constructed so that levels at which the pulse wave signal passes through said filter gradually decreases;

a pulse rate calculating means for calculating a pulse rate based on the filtered pulse wave signal; and a characteristics setting means for setting characteristics of said filter by setting the reference frequency based on the pulse rate calculated by said pulse rate calculating means.

14. The pulse wave detecting device of claim 13 wherein the level at which the pulse wave signal passes through the filter gradually decreases from a reference frequency to a lower and an upper limit frequency of a fundamental wave.

15. A pulse wave detecting device comprising:

a pulse wave detecting sensor for detecting pulse waves and outputting pulse wave signals;

a filter having variable characteristics for filtering the pulse wave signal;

a pulse rate calculating means for calculating the pulse rate based on the filtered pulse wave signal; and a characteristics setting means for setting characteristics of said filter based on the pulse rate calculated by said pulse rate calculating means;

wherein said characteristics setting means changes the characteristics set in said filter when a change in the pulse rate calculated by said pulse rate calculating means is greater than a predetermined change.

* * * * *